(12) United States Patent
Ebert

(10) Patent No.: US 10,701,350 B1
(45) Date of Patent: Jun. 30, 2020

(54) SYSTEMS AND METHODS FOR ADJUSTING HEAD-MOUNTED DISPLAYS FOR INTER-PUPILLARY DISTANCE

(71) Applicant: Oculus VR, LLC, Menlo Park, CA (US)

(72) Inventor: Ryan Michael Ebert, Kirkland, WA (US)

(73) Assignee: Facebook Technologies, LLC, Menlo Park, CA (US)

( * ) Notice: Subject to any disclaimer, the term of this patent is extended or adjusted under 35 U.S.C. 154(b) by 38 days.

(21) Appl. No.: 16/014,447

(22) Filed: Jun. 21, 2018

(51) Int. Cl.
*H04N 13/344* (2018.01)
*A61B 3/11* (2006.01)
*G02B 27/01* (2006.01)
*A61B 3/00* (2006.01)

(52) U.S. Cl.
CPC ......... *H04N 13/344* (2018.05); *A61B 3/0008* (2013.01); *A61B 3/0075* (2013.01); *A61B 3/111* (2013.01); *G02B 27/0176* (2013.01); *G02B 2027/0154* (2013.01); *G02B 2027/0161* (2013.01)

(58) Field of Classification Search
CPC .... G02B 2027/0161; G02B 2027/0163; G02B 2027/0181; G02B 27/0176; H04N 13/344; H04N 13/371
See application file for complete search history.

(56) References Cited

U.S. PATENT DOCUMENTS

| | | | | |
|---|---|---|---|---|
| 6,619,799 | B1* | 9/2003 | Blum | G02C 7/049 |
| | | | | 351/159.39 |
| 2014/0274391 | A1* | 9/2014 | Stafford | H04N 13/327 |
| | | | | 13/327 |
| 2016/0124247 | A1* | 5/2016 | Lamorte | G02C 5/045 |
| | | | | 351/46 |
| 2017/0227771 | A1* | 8/2017 | Sverdrup | G02B 5/289 |
| 2017/0237977 | A1* | 8/2017 | Patel | G02B 27/0176 |
| | | | | 348/53 |
| 2017/0289518 | A1* | 10/2017 | Kim | H04N 13/239 |
| 2018/0263488 | A1* | 9/2018 | Pamplona | A61B 3/09 |
| 2019/0018236 | A1* | 1/2019 | Perreault | G02B 27/0093 |
| 2019/0072770 | A1* | 3/2019 | Hall | G01B 5/0014 |
| 2019/0072771 | A1* | 3/2019 | Hall | G01B 5/0014 |
| 2019/0260981 | A1* | 8/2019 | Ollila | G02B 27/0172 |

\* cited by examiner

*Primary Examiner* — Viet D Pham
(74) *Attorney, Agent, or Firm* — FisherBroyles, LLP

(57) ABSTRACT

A head-mounted display apparatus may include a left display subsystem and a right display subsystem, and the left and right display subsystems may each have a display screen and a lens configured to focus light from the display screen at an exit pupil of the head-mounted display apparatus. The head-mounted display system may also include an actuation subsystem configured to change relative positioning of the left and right display subsystems based on received data indicative of an inter-pupillary distance of a user. Various other methods, systems, and devices are also disclosed.

19 Claims, 9 Drawing Sheets

SYSTEMS AND METHODS FOR ADJUSTING HEAD-MOUNTED DISPLAYS FOR INTER-PUPILLARY DISTANCE

BACKGROUND

The present disclosure generally relates to enhancing images from electronic displays, and specifically to systems and methods for adjusting a head-mounted display (HMD) system to account for an inter-pupillary distance (IPD) of a user.

A head-mounted display system can be used to simulate virtual environments (i.e., virtual reality) or to overlay visual content on a view of the real word (i.e., augmented reality). For example, stereoscopic images may be displayed on a pair of electronic displays inside an HMD to simulate the illusion of depth, and head-and-eye tracking sensors may be used to estimate which portions of the virtual environment are being viewed by a user. While some HMDs may allow a user to make manual adjustments to account for IPD, manual methods may be subject to user error and may need to be repeated each time a different user uses the HMD. What is needed, therefore, are more efficient and/or effective methods and systems for accounting for a particular user's IPD.

SUMMARY

As will be described in greater detail below, embodiments described herein may provide for automated IPD adjustment, based on identification of a distance between a user's pupils.

One or more embodiments may include a head-mounted display apparatus having a left display subsystem and a right display subsystem. The left and right display subsystems may each include a display screen and a lens configured to focus light from the display screen at an exit pupil of the head-mounted display apparatus. The head-mounted display apparatus may also include an actuation subsystem configured to change relative positioning of the left and right display subsystems based on received data indicative of an inter-pupillary distance of a user. In one example, the head-mounted display apparatus may include a detection subsystem configured to identify the inter-pupillary distance of the user while the user is wearing the head-mounted display apparatus. The actuation subsystem may be in communication with and may receive the data indicative of the inter-pupillary distance of the user from the detection subsystem. In one example, the detection subsystem may be configured to measure the inter-pupillary distance of the user while the user is wearing the head-mounted display apparatus.

In one embodiment, the detection subsystem may measure the inter-pupillary distance of the user by projecting a dot pattern onto each eye of the user, analyzing a reflection of the dot pattern from each eye of the user to identify a location of each pupil of the user, and comparing the location of each pupil of the user to calculate the inter-pupillary distance.

In at least one embodiment, the actuation subsystem of the head-mounted display apparatus may include a first actuator coupled to the left display subsystem and configured to move the left display subsystem independent of the right display subsystem. Similarly, the actuation subsystem may include a second actuator coupled to the right display subsystem and configured to move the right display subsystem independent of the left display subsystem. In one example, the actuation subsystem may include a single actuator configured to move the left and right display subsystems at least substantially simultaneously. In another example, the actuation subsystem may include a motor and a drive mechanism that couples the motor to at least one of the left and right display subsystems such that driving by the motor causes the drive mechanism to move at least one of the left and right display subsystems. In this example, the motor may change the relative positioning by causing the drive mechanism to move at least one of the left and right display subsystems.

In one example, the motor may include a stepper motor. In a further example, the drive mechanism may include a pinion secured to the motor and a rack driven by the pinion and secured to the at least one of the left and right display subsystems to which the drive mechanism is coupled. In another example, a left portion of the drive mechanism may have a first thread that interfaces with the left display subsystem and a right portion of the drive mechanism may have a second thread that interfaces with the right display subsystem. In such examples, the second thread may include a helix that twists in an opposite direction of a helix of the first thread such that rotation of the drive mechanism moves the left and right display subsystems in opposite directions.

In a further example, each of the left and right display subsystems may include a varifocal subsystem configured to move the display screen relative to the lens to change a focal length of the lens. In another example, the head-mounted display apparatus may include a linear track positioned to guide lateral movement of at least one of the left and right display subsystems as the actuation subsystem changes the relative positioning of the left and right display subsystems. In a further example, the head-mounted display apparatus may include a nonlinear track positioned to guide angular movement of at least one of the left and right display subsystems as the actuation subsystem changes the relative positioning of the left and right display subsystems. In at least one embodiment, the head-mounted display apparatus may include an actuation subsystem that changes the relative positioning of the left and right display subsystems by rotating at least one of the left and right display subsystems.

In another embodiment, the head-mounted display apparatus may include a housing within which the left and right display subsystems are disposed. In such examples, the actuation subsystem may include an actuator mounted to the housing and a drive mechanism coupled to the actuator and to at least one of the left display subsystem and the right display subsystem.

A further embodiment may include a method having at least the steps of identifying an inter-pupillary distance of a user of a head-mounted display apparatus and directing an actuation subsystem to change relative positioning of left and right display subsystems of the head-mounted display apparatus based on the identified inter-pupillary distance of the user. In such examples, the left and right display subsystems each may include a display screen and a lens configured to focus light from the display screen at an exit pupil of the head-mounted display apparatus. In one example, identifying the inter-pupillary distance may include measuring the inter-pupillary distance of the user while the user is wearing the head-mounted display apparatus.

In another example, measuring the inter-pupillary distance may include directing an illumination source to project a dot pattern onto each eye of the user, analyzing a reflection of the dot pattern from each eye of the user to identify a location of each pupil of the user, and comparing the location of each pupil of the user to calculate the interpupillary distance. In a further example, the actuation subsystem may include a first actuator coupled to the left display subsystem and configured to move the left display subsystem independent of the right display subsystem. The actuation subsystem may also include a second actuator coupled to the right display subsystem and configured to move the right display subsystem independent of the left display subsystem.

A further embodiment may include securing left and right display subsystems to a housing of a head-mounted display apparatus, where each of the left and right display subsystems may include a display screen and a lens configured to focus light from the display screen at an exit pupil of the head-mounted display apparatus. Such embodiments may also include coupling, to at least one of the left and right display subsystems, an actuation subsystem configured to change relative positioning of the left and right display subsystems based on received data indicative of an interpupillary distance of a user.

Features from any of the above-mentioned embodiments may be used in combination with one another in accordance with the general principles described herein. These and other embodiments, features, and advantages will be more fully understood upon reading the following detailed description in conjunction with the accompanying drawings and claims.

BRIEF DESCRIPTION OF THE DRAWINGS

The accompanying drawings illustrate a number of exemplary embodiments and are a part of the specification. Together with the following description, these drawings demonstrate and explain various principles of the instant disclosure.

Figure 1:
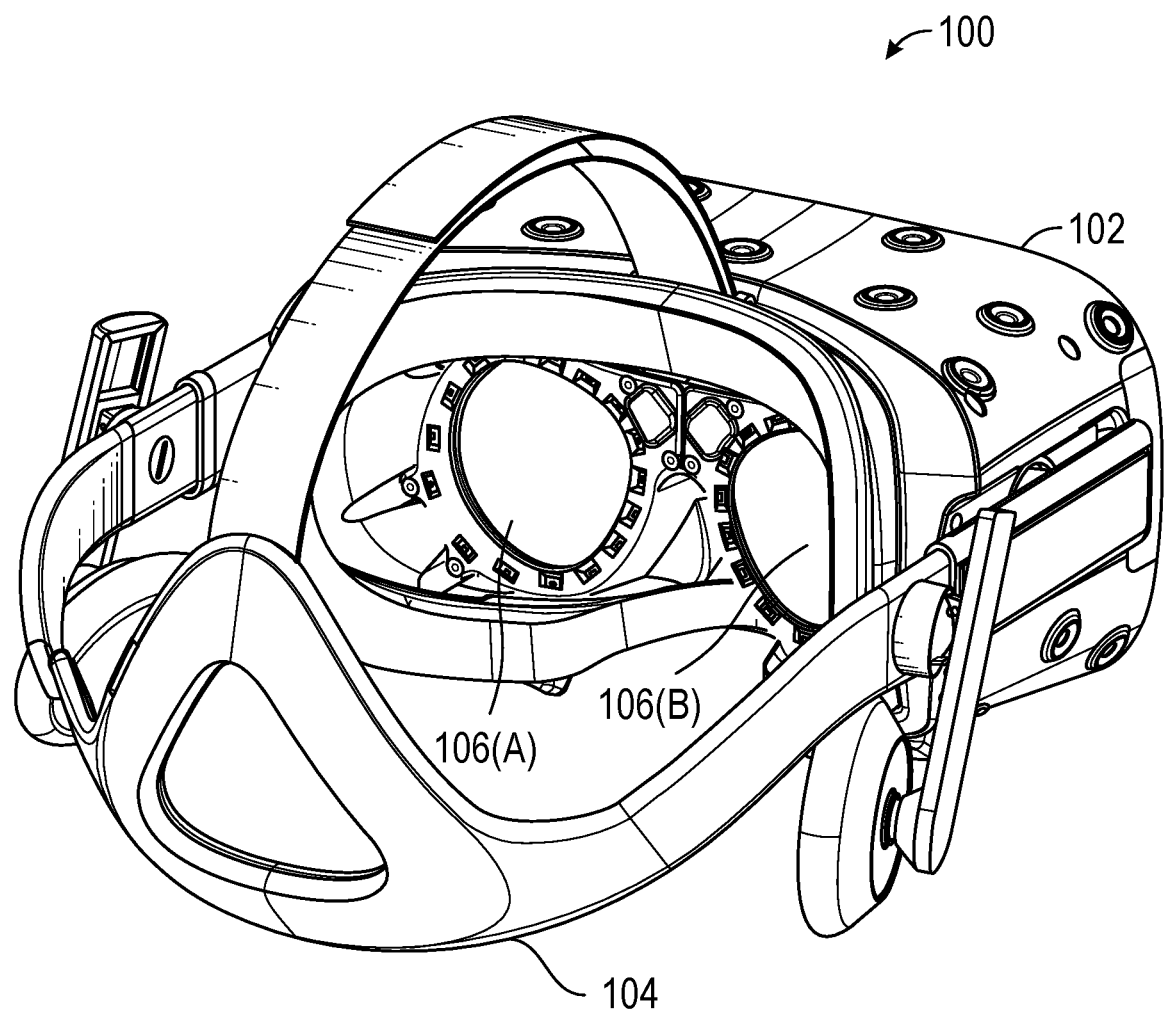
FIG. 1 depicts a head mounted display, in accordance with at least one embodiment.

Throughout the drawings, identical reference characters and descriptions indicate similar, but not necessarily identical, elements. While the exemplary embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION OF EXEMPLARY EMBODIMENTS

The present disclosure is generally directed to automated IPD adjustments for head-mounted displays (HMDs). As will be explained in greater detail below, embodiments described herein may automate IPD adjustments based on information about a distance between the pupils of a user's eyes. These embodiments may provide several benefits, such as ease of use for an individual user (no need to manually set an IPD), ease of use for multiple users (no need to reset the IPD each time an HMD is used by a different user), and accuracy of adjustment (users who adjust for IPD manually may under- or over-estimate the correct IPD adjustment). Moreover, in some examples, the systems and methods described herein may recognize a user (e.g., by eye patterns, entered password, etc.), recall the user's IPD from memory, and quickly set the correct IPD without the need to recalculate the IPD.

Figure 2:
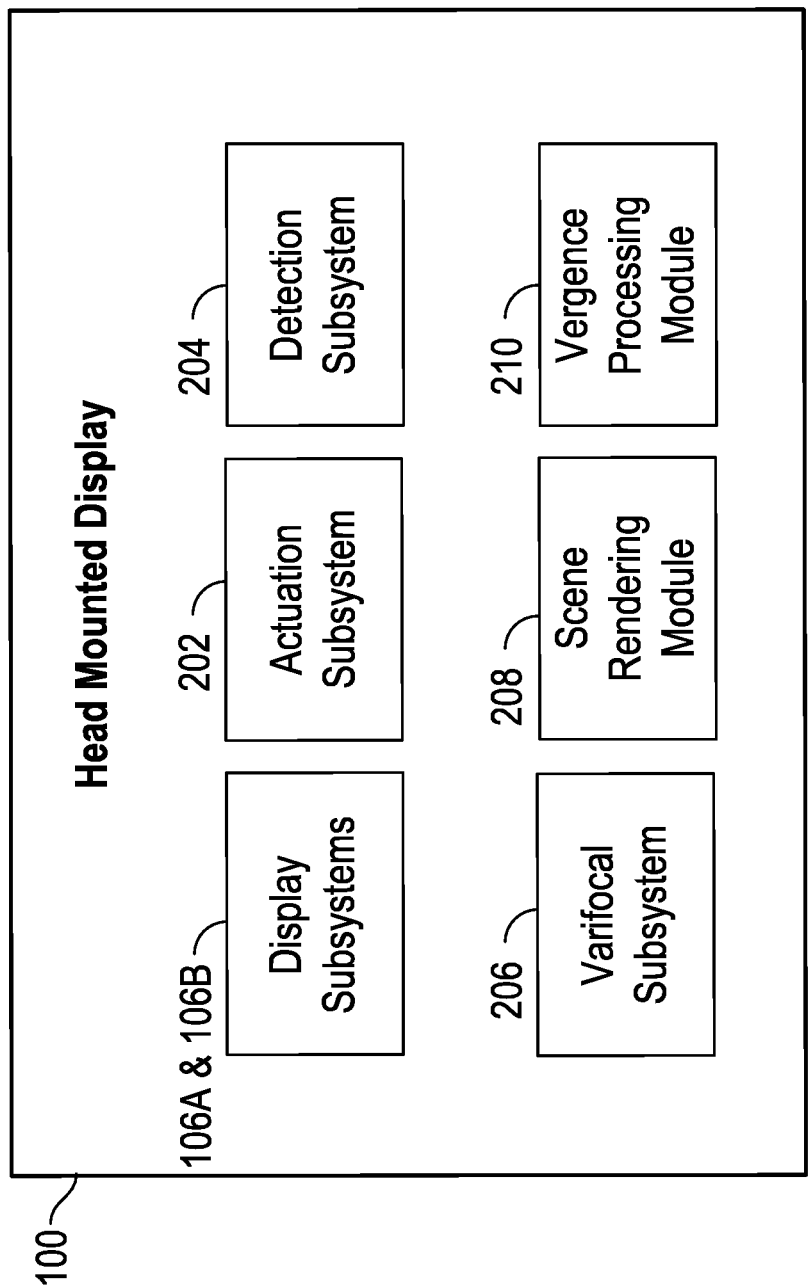
FIG. 2 shows an example virtual reality system, in accordance with at least one embodiment.

The following will provide, with reference to FIGS. 1-2, a description of an HMD system in which one or more embodiments described herein may be implemented. The discussion associated with FIG. 3 describes an example of a display subsystem of an embodiment. The discussion corresponding to FIG. 4 provides a discussion of making automated IPD adjustments to left and right display subsystems. Furthermore, the discussion associated with FIGS. 5-11 will provide examples of IPD adjustment configurations corresponding to various embodiments. In addition, the discussion corresponding to FIG. 12 describes steps of a method for making automated adjustments to account for a user's IPD, and the discussion corresponding to FIG. 13 depicts steps of a method for assembling a system for making automated adjustments to account for a user's IPD.

Turning now to FIG. 1, an HMD 100 may include a front rigid body 102 and a band 104 dimensioned to be positioned around a user's head. HMD 100 may be a virtual-reality system, an augmented-reality system, a mixed-reality system, or some combination thereof. The front rigid body 102 may include a left display subsystem 106(A) and a right display subsystem 106(B) positioned in front of one or more electronic display elements. Left display subsystem 106(A) may include a left display screen and a left lens configured to focus light from the display screen at an exit pupil of HMD 100. Similarly, right display subsystem 106(B) may include a right display screen a right lens configured to focus light from the display screen at an exit pupil of HMD 100.

Display subsystems 106(A) and 106(B) may be configured in any suitable manner. For example, the lenses of display subsystems 106(A) and 106(B) may direct light from a display to an exit pupil for viewing by a user using one or more optical elements, such as apertures, Fresnel lenses, convex lenses, concave lenses, filters, and so forth, and may include combinations of various different optical elements. In some embodiments, one or more optical elements in display subsystems 106(A) and 106(B) may have one or more coatings, such as anti-reflective coatings. Magnification of the image light by the optical elements may allow for the electronic display to be physically smaller, weigh less, and consume less power than larger displays. Additionally, magnification of the image light may increase a field of view of the displayed content. For example, the field of view of the displayed content may be such that the displayed content is presented using almost all (e.g., 150 degrees diagonal), and in some cases all, of the user's field of view.

As shown in FIG. 2, HMD 100 may also include a variety of other components. For example, HMD 100 may include an actuation subsystem 202 configured to change relative positioning of left and right display subsystems 106(A) and 106(B) based on received data indicative of an inter-pupillary distance of a user. Actuation subsystem 202 may receive the data via user input, via an eye-tracking system or other detection system, or in any other suitable manner. Actuation subsystem 202 may include a first actuator coupled to left display subsystem 106(A) to move left display subsystem 106(A) independent of right display subsystem 106(B). Actuation subsystem 202 may also include a second actuator coupled to right display subsystem 106(B) and configured to move right display subsystem 106(B) independent of left display subsystem 106(A). Actuation subsystem 202 may be configured in any suitable manner, as discussed in greater detail in the disclosure corresponding to FIGS. 5-11.

HMD 100 may also include a detection subsystem 204 configured to identify the inter-pupillary distance of a user while the user is wearing HMD 100. Actuation subsystem 202 may be communicatively coupled to detection subsystem 204 and may receive the data indicative of the inter-pupillary distance of a user from detection subsystem 204. In some embodiments, detection subsystem 204 may measure and/or calculate the inter-pupillary distance of the user while the user is wearing the HMD 100. For example, detection subsystem 204 may detect the positions of a user's eyes and may use this information to calculate the user's IPD.

Detection subsystem 204 may track eye position and/or eye movement of a user of HMD 100 in a variety of ways. A camera or other optical sensor inside HMD 100 may capture image information of a user's eyes, and detection subsystem 204 may use the captured information to determine inter-pupillary distance, interocular distance, a three-dimensional (3D) position of each eye relative to HMD 100 (e.g., for distortion adjustment purposes), including a magnitude of torsion and rotation (i.e., roll, pitch, and yaw), and/or gaze directions for each eye. In one example, infrared light may be emitted within HMD 100 and reflected from each eye. The reflected light may be received or detected by the camera and analyzed to extract eye rotation data from changes in the infrared light reflected by each eye. Any other suitable method for tracking the eyes of a user can be used by detection subsystem 204. For example, a light source (e.g., infrared light-emitting diodes) may emit a dot pattern onto each eye of the user. Detection subsystem 204 may then detect (e.g., via an optical sensor) and analyze a reflection of the dot pattern from each eye of the user to identify a location of each pupil of the user.

Accordingly, detection subsystem 204 may track up to six degrees of freedom of each eye (i.e., 3D position, roll, pitch, and yaw) and at least a subset of the tracked quantities may be combined from two eyes of a user to estimate a gaze point (i.e., a 3D location or position in the virtual scene where the user is looking) and/or an IPD.

Further, distance between a pupil and a display subsystems may change as the eye moves to look in different directions. The varying distance between a pupil and a display subsystem as viewing direction changes may be referred to as "pupil swim" and may contribute to distortion perceived by the user as a result of light focusing in different locations as the distance between the pupil and the display subsystem changes. Accordingly, measuring distortion at different eye positions and pupil distances relative to display subsystems and generating distortion corrections for different positions and distances may allow mitigation of distortion caused by "pupil swim" by tracking the 3D position of a user's eyes and applying a distortion correction corresponding to the 3D position of each of the user's eyes at a given point in time. Thus, knowing the 3D position of each of a user's eyes may allow for the mitigation of distortion caused by changes in the distance between the pupil of the eye and display subsystems 106 by applying a distortion correction for each 3D eye position. Furthermore, as noted above, knowing the position of each of the user's eyes may also enable detection subsystem 204 to make automated adjustments for a user's IPD.

In some embodiments, HMD 100 may include a variety of additional subsystems that may work in conjunction with detection subsystem 204 and actuation subsystem 202. For example, HMD 100 may include a varifocal actuation subsystem 206, a scene-rendering module 208, and a vergence processing module 210. Varifocal subsystem 206 may cause left and right display subsystems 106(A) and 106(B) to vary the focal distance of HMD 100. In one embodiment, varifocal subsystem 206 may physically change the distance between an electronic display and the optics through which it is viewed by moving the display, the optics, or both. Additionally, moving or translating two lenses relative to each other may also be used to change the focal distance of HMD 100. Thus, varifocal subsystem 206 may include actuators or motors that move displays and/or optics to change the distance between them. Varifocal subsystem 206 may be separate from or integrated into display subsystems 106(A) and 106(B) in various embodiments. Varifocal subsystem 204 may also be integrated into or separate from actuation subsystem 202 and/or detection subsystem 204.

Vergence processing module 210 may determine a vergence depth of a user's gaze based on the gaze point and/or an estimated intersection of the gaze lines determined by detection subsystem 204. Vergence may be the simultaneous movement or rotation of both eyes in opposite directions to maintain single binocular vision, which may be naturally and automatically performed by the human eye. Thus, a location where a user's eyes are verged is where the user is looking and is also typically the location where the user's eyes are focused. For example, vergence processing module 210 may triangulate the gaze lines to estimate a distance or depth from the user associated with intersection of the gaze lines. The depth associated with intersection of the gaze lines can then be used as an approximation for the accommodation distance, which identifies a distance from the user where the user's eyes are directed. Thus, the vergence distance allows determination of a location where the user's eyes should be focused and a depth from the user's eyes at which the eyes are focused, thereby providing information such as an object or plane of focus, for rendering adjustments to the virtual scene.

Vergence processing module 210 may coordinate with actuation subsystem 202 and/or detection subsystem 204 to make adjustments to display subsystem 106 to account for a user's vergence depth. When the user is focused on something at a distance, the user's pupils may be slightly farther apart than when the user is focused on something close. Detection subsystem 204 may receive information about the user's vergence or focus depth and may adjust display subsystems 106(A) and 106(B) to be closer together when the user's eyes focus or verge on something close and to be farther apart when the user's eyes focus or verge on something at a distance.

Scene-rendering module 208 may receive content for a virtual scene and provide the content for display by display subsystems 106(A) and 106(B). Additionally, scene-rendering module 208 may adjust the content based on information from vergence processing module 210. For example, upon receiving the content from a graphics engine, scene-rendering module 208 may adjust the content based on the predicted state (i.e., eye position and focal distance) of display subsystems 106(A) and 106(B) received from detection subsystem 204 by adding a correction or pre-distortion into rendering of the virtual scene to compensate or correct for the distortion caused by the predicted state of display subsystems 106(A) and 106(B). Scene-rendering module 208 may also add depth-of-field blur based on the user's gaze, vergence depth (or accommodation depth) received from vergence processing module 210, and/or measured properties of the user's eye (e.g., 3D position of the eye, etc.). Additionally, scene-rendering module 208 may determine a portion of the content to be displayed on electronic displays within display subsystems 106(A) and 106(B) based on a variety of input data. In some embodiments, scene-rendering module 208 may coordinate with detection subsystem 204 and actuation subsystem 202 to determine whether a scene would cause a user's eyes to focus or verge on something that is close or far away, and actuation subsystem 202 may adjust display subsystems 106(A) and 106(B) accordingly.

Figure 3:
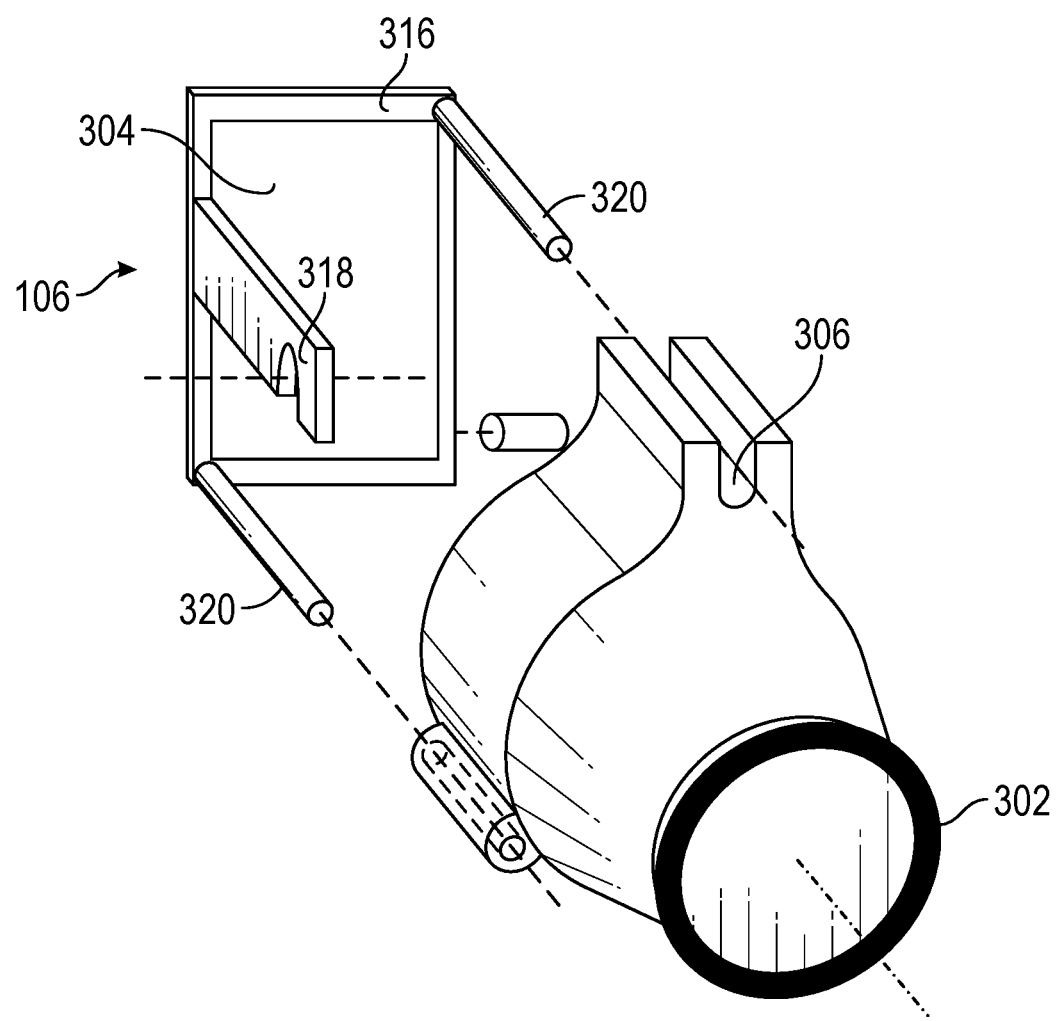
FIG. 3 depicts an example of a display subsystem of an embodiment.
Figure 4:
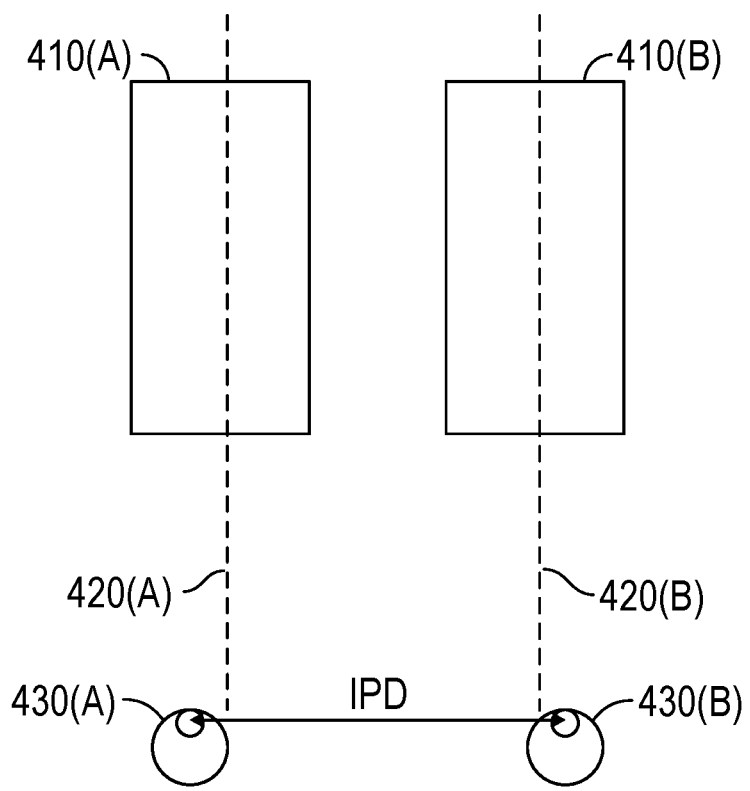
FIG. 4 illustrates IPD adjustment of left and right display subsystems.

FIG. 3 depicts an example of left display subsystem 106(A) configured for use with varifocal subsystem 206. In the implementation depicted in FIG. 3, an optics subsystem 302 may be fixed within HMD 100, and an electronic display 304 may be moved relative to optics subsystem 302 based on a determined vergence depth. Electronic display 304 may be mounted to a display bracket 316 that may include display bracket arm 318 and/or guide pins 320. Display bracket arm 318 may receive or engage a push pin, for example, of a drive mechanism (not shown) and guide pins 320 may slide freely within guides 306. Thus, the push pin may engage display bracket arm 318 and move display bracket 316 that supports electronic display 304, and guide pins 320 may guide the movement of electronic display 304 relative to optics subsystem 302 by engaging guides 306 of optics subsystem 302.

As discussed above, varifocal subsystem 206 may dynamically vary the focus depth to bring images presented to a user wearing HMD 100 into focus, which may keep the user's eyes in a zone of comfort as vergence and accommodation change. Additionally, eye tracking in combination with the variable focus of the varifocal system may allow blurring to be introduced as depth cues in images presented by HMD 100.

Detection subsystem 204 may be integrated into and/or function in coordination with varifocal actuation subsystem 206 to move one or more optical components to account for user's IPD. Detection subsystem 204 may receive or identify inter-pupillary distance information and use that information to control one or more actuators to change relative positions of a left display subsystem and a right display subsystem in a manner that results in the distance between the optical axes of the display subsystems being aligned with the optical axis of pupils of the user's eyes, within a configurable tolerance. Detection subsystem 204 also may receive information from another subsystem or external computing device regarding a user's IPD. That information may be used to calculate the relative positions of the display subsystems at which optical axis of both display systems are aligned with the user's pupils.

FIG. 4 illustrates an example of left and right display subsystems that may be adjusted to accommodate a user's IPD. As shown in FIG. 4, an optical axis 420(A) of a left display subsystem 410(A) may not be aligned with a pupil of a user's left eye 430, and an optical axis 420(B) of a left display subsystem 410(B) may not be aligned with a user's right eye 430(B). To improve a viewing experience, detection subsystem 204 may move left display subsystem 410 (A) to the left such that optical axis 420(A) aligns with the pupil of the user's left eye 430(A), and detection subsystem 204 may move right display subsystem 410(B) to the right such that optical axis 420(B) aligns with the pupil of the user's right eye 430(B). In this manner, detection subsystem 204 may adjust display subsystems 410(A) and 410(B) to account for the user's IPD.

Figure 5:
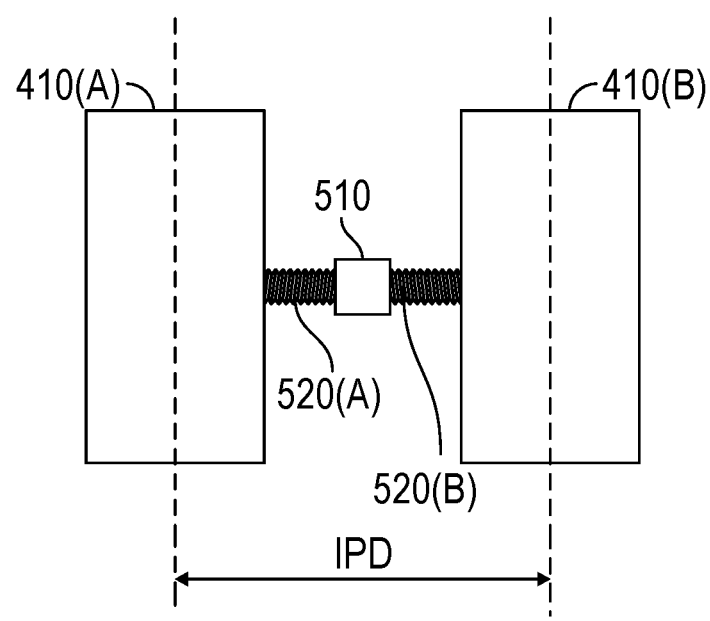
FIG. 5 depicts IPD adjustment using a motor and two lead screws mounted to and located between left and right display subsystems.

FIGS. 5-12D depict various examples of actuation subsystem 202. FIG. 5 depicts an actuation subsystem having a motor 510 and, as a drive mechanism, two lead screws 520(A) and 520(B) mounted to and located between left and right display subsystems 410(A) and 410(B). Motor 510 (e.g., a stepper motor) may be connected to lead screws 520(A) and 520(B) on each side, which in turn may be connected to left and right displays 410(A) and 410(B). In an embodiment, the two lead screws 520(A) and 520(B) may be threaded in opposite directions (i.e., one thread may include a helix that twists in an opposite direction of a helix of the other thread such that each lead screw is reverse threaded relative to the other) so that motor 510 moves the left and right display subsystems simultaneously in opposite directions. Under the control of detection subsystem 204, motor 510 may adjust the relative positioning of the two display subsystems 410(A) and 410(B) until both optical axes are aligned with the user's pupils at the user's eyes. Thus, motor 510 may function as a single actuator configured to move the left and right display subsystems at least substantially simultaneously.

A stepper motor is only one example of an actuation subsystem that may be used in an embodiment in conjunction with an IPD adjustment subsystem to adjust the distance between the optical axes of the left and right display subsystems. As will be clear to those skilled in the art, any other suitable type of motor or other actuation subsystem may be used in conjunction with the IPD adjustment subsystem embodiments described herein. Examples of such actuation systems may include, but are not limited to, a power screw and nut sled, a cam and roller, a face cam of varying thickness that pushes against a push contact roller to move the electronic display, a pivoting arm to move a display bracket supporting the electronic display, a gear and rack (rack and pinion) implementation, a cable or belt drive with one or more pulleys, a solenoid motor, a voice coil actuator motor, an alternating north-south poled shaft with a solenoid-like driving coil, piezo bending and pneumatic actuation, a flexure-based guidance method, a pin and shaft guidance method, a scissor linkage method, a Sarrus linkage guidance method, etc.

Figure 6:
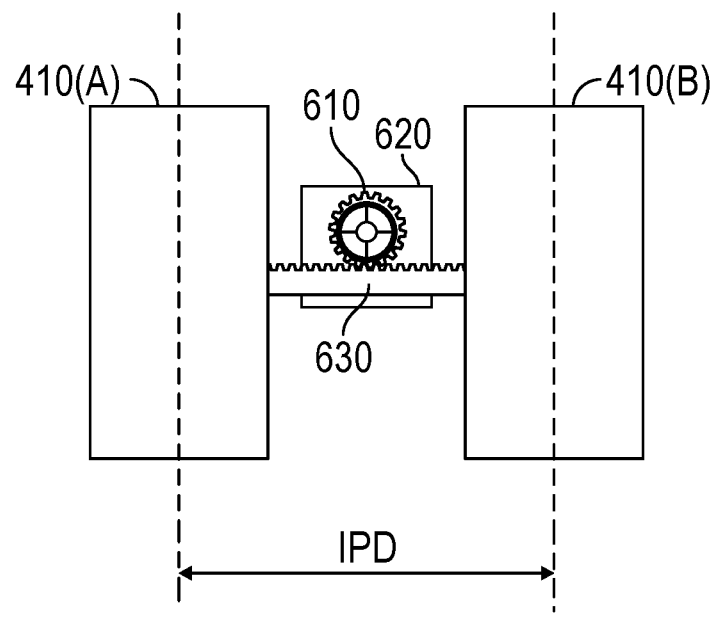
FIG. 6 depicts IPD adjustment using a gear and rack (rack and pinion) mounted to left and right display subsystems.

FIG. 6 depicts IPD adjustment using an actuation subsystem including a gear 610 and a rack 630 (i.e., a rack and pinion) mounted to left and right display subsystems 410(A) and 410(B). Gear 610 may be driven by a motor 620, and rotation of gear 610 along rack 630 (which may have two components) may change the distance between left and right display subsystems 410(A) and 410(B). Under the control of actuation subsystem 202, motor 620 may adjust the relative positioning of left and right display subsystems 410(A) and 410(B) until both optical axes are aligned with the user's pupils.

Figure 7:
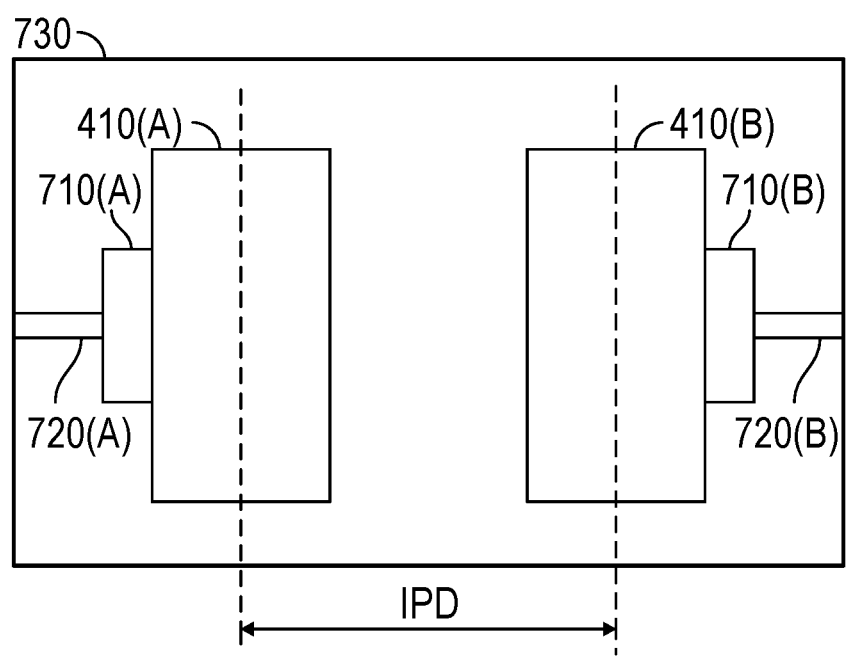
FIG. 7 depicts IPD adjustment using two motors mounted to left and right display subsystems and connected by lead screws to a housing.

FIG. 7 depicts an actuation subsystem including two motors 710 mounted to left and right display subsystems 410(A) and 410(B) and connected by drive mechanisms 720(A) and 720(B) to a housing 730. One motor 710(A) may be mounted to a left side of left display subsystem 410(A) and connected by drive mechanism 720(A) to housing 730. Another motor 710(B) may be mounted to a right side of right display subsystem 410(B) and connected by drive mechanism 720(B) to housing 730. Under the control of actuation subsystem 202, each motor 710 may adjust the distance between its corresponding display subsystem and housing 730, thereby adjusting the relative positioning of the two display subsystems 410(A) and 410(B) until both optical axes are aligned with the user's pupils at the user's eyes. The configuration shown in FIG. 7 may enable IPD subsystem 212 to account for a position of each eye of a user independently, which may be beneficial for aligning display subsystems 410(A) and/or 410(B) for a user with facial asymmetries.

Figure 8:
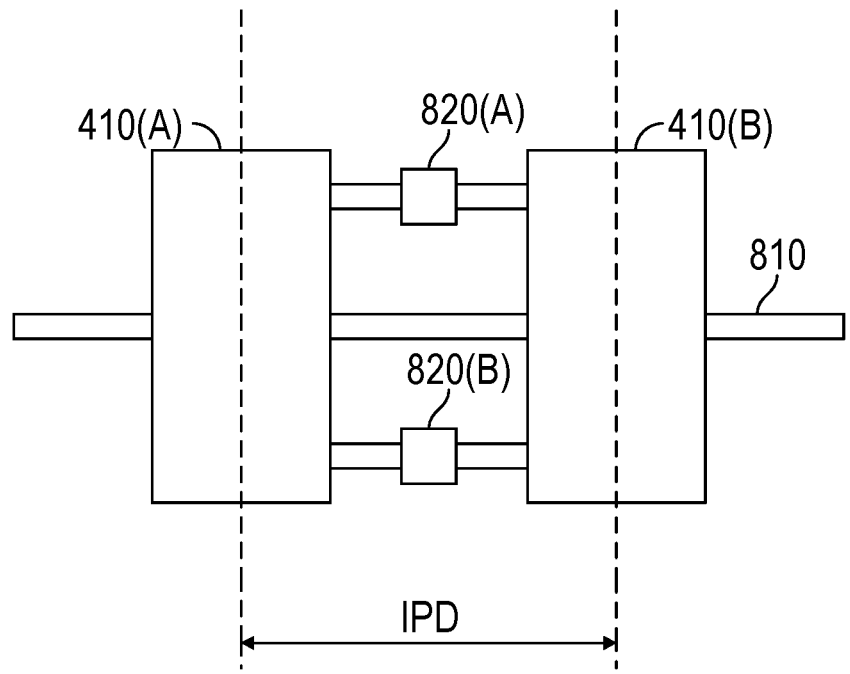
FIG. 8 depicts IPD adjustment using two motors, each with two lead screws, mounted to and located between left and right display subsystems constrained to travel along a linear guide.

FIG. 8 depicts an actuation subsystem having two motors 820, each with two drive mechanisms (e.g., lead screws), mounted to and located between left and right display subsystems 410(A) and 410(B) constrained to travel along a linear guide 810. In this embodiment, motors 820(A) and 820(B) may function essentially the same as motor 510 in FIG. 5. However, the two display subsystems 410(A) and 410(B) may be constrained to travel along a linear track or guide 810 to provide added stability and to reduce stress on the lead screws. Under the control of detection subsystem 204, motors 820(A) and 820(B) may adjust the relative positioning of the two display subsystems 410(A) and 410(B) until both optical axes of the display subsystems are aligned with the user's pupils.

Figure 9:
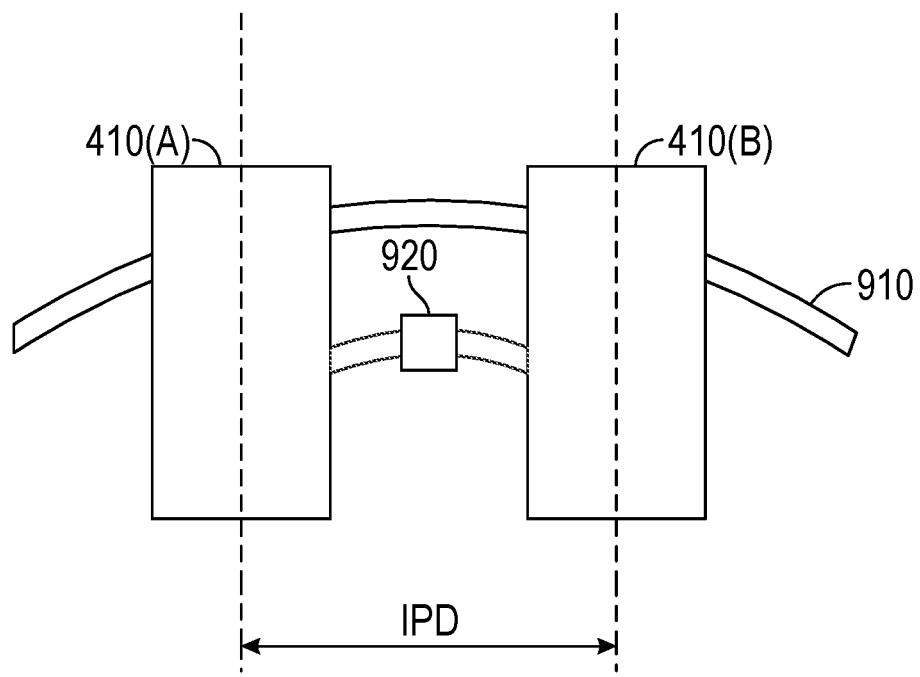
FIG. 9 depicts IPD adjustment using one motor and two curved lead screws, mounted to and located between left and right display subsystems constrained to travel along a curved guide.

FIG. 9 depicts an actuation subsystem that uses one motor 920 and two curved drive mechanisms, mounted to and located between left and right display subsystems 410(A) and 410(B) and constrained to travel along a curved guide 910. In this embodiment, motor 920 may function essentially the same as motor 510 in FIG. 5. However, the two display subsystems 410(A) and 410(B) may be constrained to travel along a non-linear, curved guide 910 to provide added stability and to reduce stress on the drive mechanisms (which also may be curved). Under the control of detection subsystem 204, motor 920 may adjust the relative positioning of the two display subsystems 410(A) and 410(B) until both optical axes are aligned with the user's pupils.

In the embodiment depicted in FIG. 9, left and right display subsystems 410(A) and 410(B) may be rotated as they travel along the curved guide 910. In another embodiment, the two display subsystems 410(A) and 410(B) may each be rotated about corresponding fixed axes (for example, by a motor driving a belt connected to a pulley or gear mounted to each display subsystem), under control of detection subsystem 204, to adjust the relative positioning of the two display subsystems 410(A) and 410(B) until both optical axes are aligned with the user's pupils at the user's eyes.

More generally, in addition to (and/or in combination with) lateral movement, detection subsystem 204 may control rotational movement of left and right display subsystems 410(A) and 410(B) until both optical axes are aligned with the user's pupils.

Figure 10:
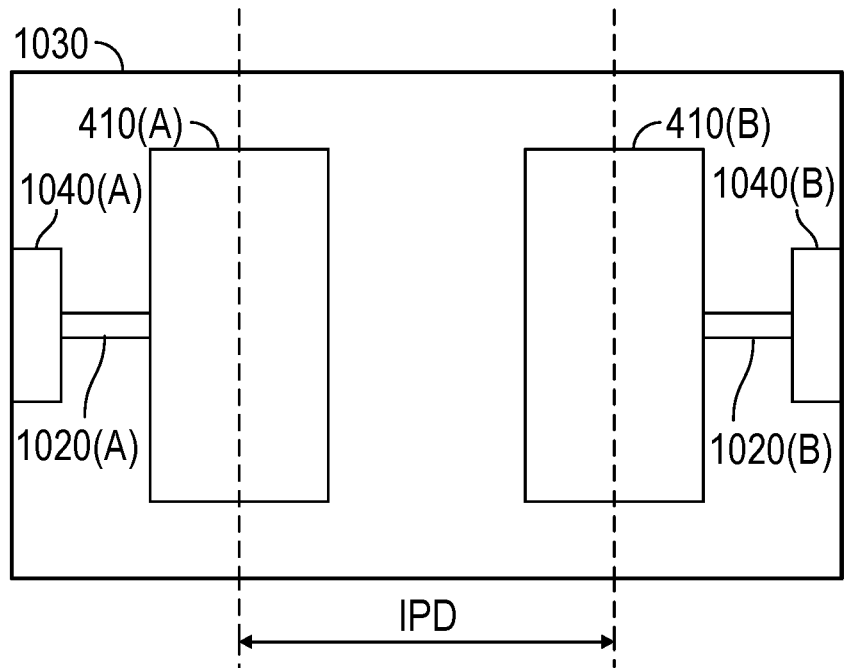
FIG. 10 depicts IPD adjustment using two motors mounted to a housing and connected by lead screws to left and right display subsystems.

FIG. 10 depicts an IPD adjustment mechanism using two motors 1040 mounted to housing 1030 and connected by lead screws 1020(A) and 1020(B) to left and right display subsystems 410(A) and 410(B). One motor 1040(A) may be mounted to housing 1030 and connected by lead screw 1020(A) to a left side of left display subsystem 410(A). Another motor 1040(B) may be mounted to housing 1030 and connected by lead screw 1020(B) to a right side of right display subsystem 410(B). Under the control of detection subsystem 204, each of motors 1040(A) and 1040(B) may adjust the distance between its corresponding display subsystem and the housing 1030, thereby adjusting the relative positioning of the two display subsystems 410(A) and 410(B) until the distance between the optical axes at the user's eyes matches the user's IPD.

Figure 11:
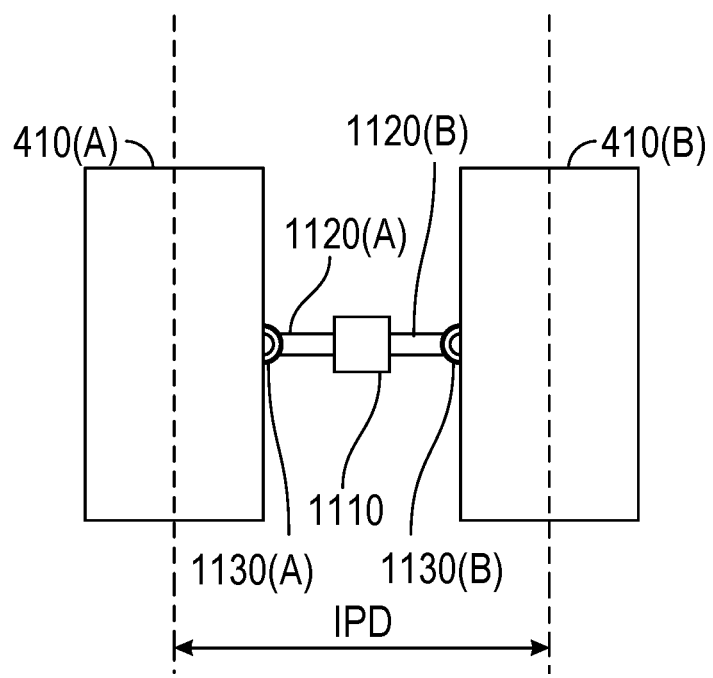
FIG. 11 depicts IPD adjustment using a motor and two lead screws mounted to and located between left and right display subsystems, wherein the lead screws are connected to the displays via hinges.

FIG. 11 depicts an actuation mechanism having a motor 1110 and two drive mechanisms 1120(A) and 1120(B) mounted to and located between left and right display subsystems 410(A) and 410(B). In this example, drive mechanisms 1120(A) and 1120(B) may include hinges 1130(A) and 1130(B) that provide added alignment flexibility. Under the control of detection subsystem 204, actuation subsystem 204 may adjust the relative positioning of display subsystems 410(A) and 410(B) until the distance between the optical axes at the user's eyes matches the user's IPD.

Figure 12:
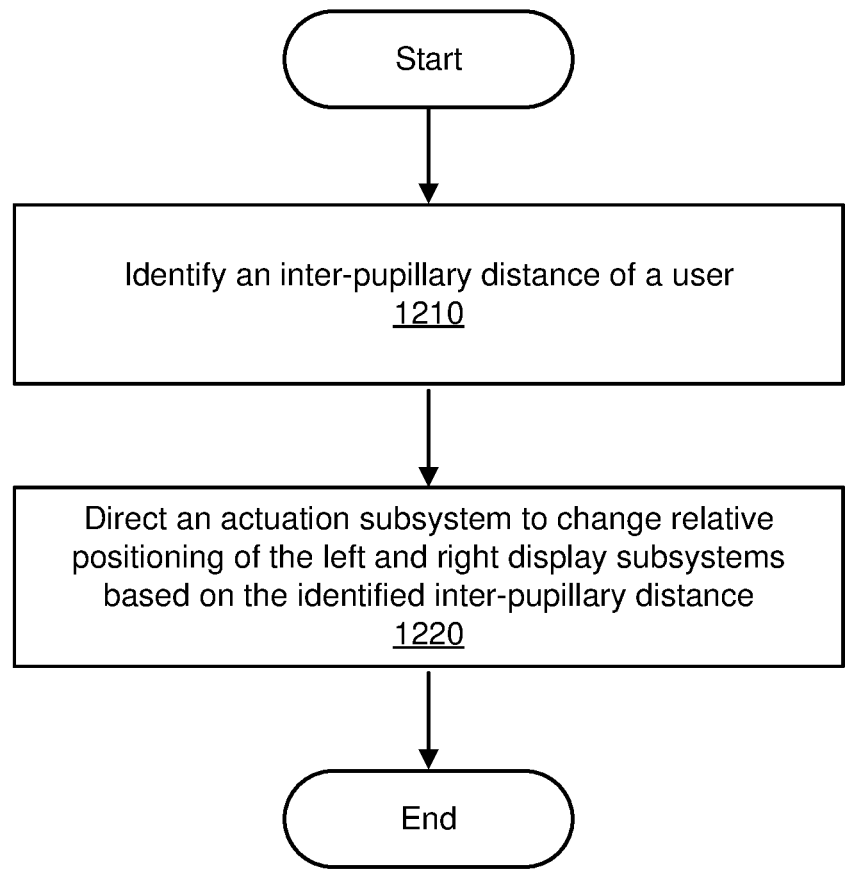
FIG. 12 depicts steps of a method for making automated adjustments to account for a user's IPD.
Figure 13:
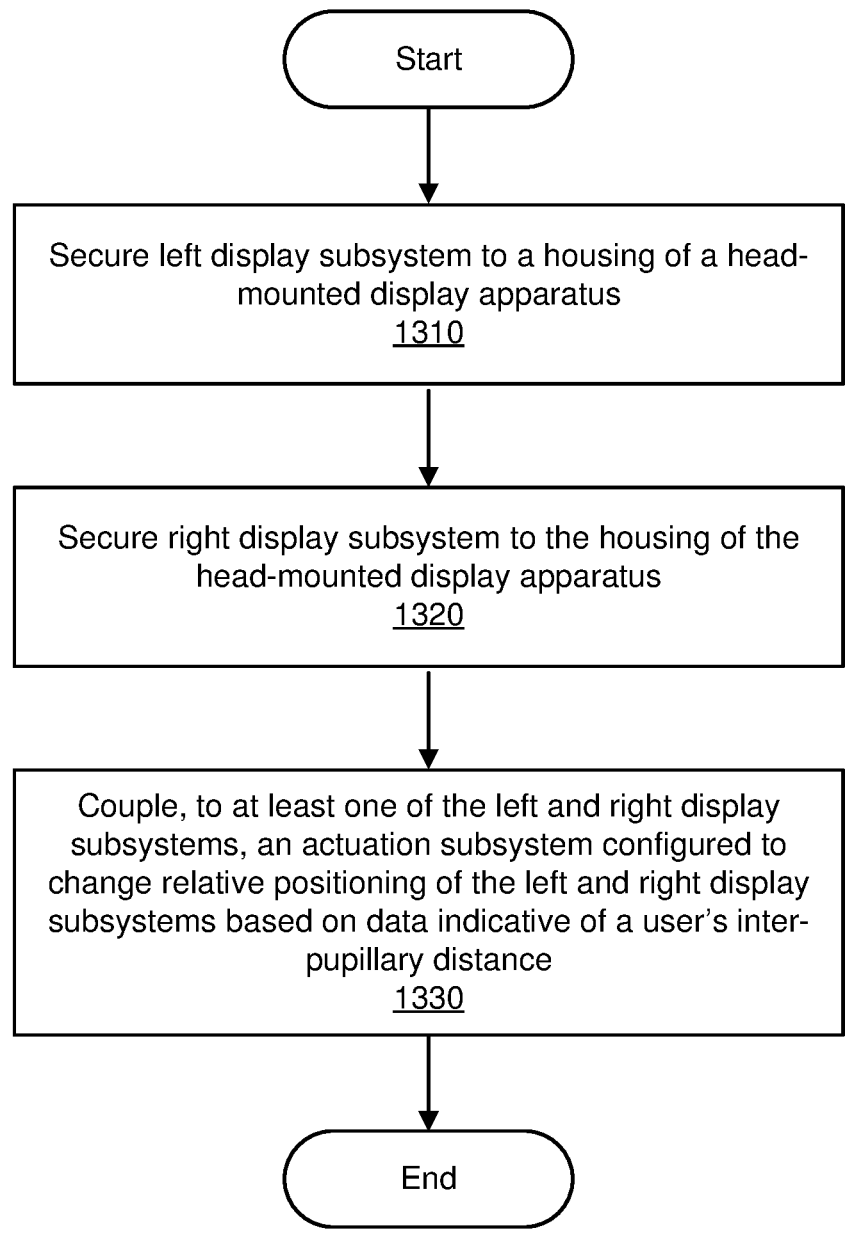
FIG. 13 depicts steps of a method for assembling a system for making automated adjustments to account for a user's IPD.

FIG. 12 is a flow diagram of an example computer-implemented method 1200 for automating adjustments to account for a user's IPD. The steps shown in FIG. 12 may be performed by any suitable computer-executable code and/or computing system, including HMD 100. In one example, each of the steps shown in FIG. 12 may represent an algorithm whose structure includes and/or is represented by multiple sub-steps, examples of which will be provided in greater detail below.

As illustrated in FIG. 12, at step 1210 one or more of the systems described herein may identify an IPD of a user. Identifying an IPD may involve any suitable process. For example, detection subsystem 204 may identify the locations of each pupil of the user's eyes. This may be done, for example, using the methods described above. Detection subsystem 204 may then calculate the IPD of the user based on the locations of the user's pupils.

At step 1220, one or more of the systems described herein may direct an actuation subsystem to change relative positioning of left and right display subsystems based on the identified IPD. For example, detection subsystem 204 may direct actuation subsystem 202 to move either or both of the left and right display subsystems to change their positioning relative to each other.

FIG. 13 illustrates a method 1300 of assembling a system that provides automated adjustments for IPD. Steps 1310 and 1320 may include securing left and right display subsystems to a housing of a head-mounted display apparatus. Step 1330 may include coupling, to at least one of the left and right display subsystems, an actuation subsystem configured to change relative positioning of the left and right display subsystems based on received data indicative of an IPD of a user. The received data may include instructions from a detection subsystem 204.

Embodiments described herein may provide for automated IPD adjustment, based on automated determination of a distance between a user's eye pupils. These embodiments provide several benefits, such as ease of use for an individual user (no need to manually set IPD), ease of use for multiple users (no need to re-set the IPD each time an HMD is used by a different user), and accuracy of adjustment (user who adjust IPD manually may under-or over-estimate the correct IPD adjustment). Moreover, the system may recognize a user (by eye patterns, entered password, etc.), recall that user's IPD from a memory, and quickly set the correct IPD without the need to recalculate the IPD.

As detailed above, the computing devices and systems described and/or illustrated herein broadly represent any type or form of computing device or system capable of executing computer-readable instructions, such as those contained within the modules described herein. In their most basic configuration, these computing device(s) may each include at least one memory device and at least one physical processor.

In some examples, the term "memory device" generally refers to any type or form of volatile or non-volatile storage device or medium capable of storing data and/or computer-readable instructions. In one example, a memory device may store, load, and/or maintain one or more of the modules described herein. Examples of memory devices include, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In some examples, the term "physical processor" generally refers to any type or form of hardware-implemented processing unit capable of interpreting and/or executing computer-readable instructions. In one example, a physical processor may access and/or modify one or more modules stored in the above-described memory device. Examples of physical processors include, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the modules described and/or illustrated herein may represent portions of a single module or application. In addition, in certain embodiments one or more of these modules may represent one or more software applications or programs that, when executed by a computing device, may cause the computing device to perform one or more tasks. For example, one or more of the modules described and/or illustrated herein may represent modules stored and configured to run on one or more of the computing devices or systems described and/or illustrated herein. One or more of these modules may also represent all or portions of one or more special-purpose computers configured to perform one or more tasks.

In some embodiments, the term "computer-readable medium" generally refers to any form of device, carrier, or medium capable of storing or carrying computer-readable instructions. Examples of computer-readable media include, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

Embodiments of the instant disclosure may include or be implemented in conjunction with an artificial reality system. Artificial reality is a form of reality that has been adjusted in some manner before presentation to a user, which may include, e.g., a virtual reality (VR), an augmented reality (AR), a mixed reality (MR), a hybrid reality, or some combination and/or derivatives thereof. Artificial reality content may include completely generated content or generated content combined with captured (e.g., real-world) content. The artificial reality content may include video, audio, haptic feedback, or some combination thereof, any of which may be presented in a single channel or in multiple channels (such as stereo video that produces a three-dimensional effect to the viewer). Additionally, in some embodiments, artificial reality may also be associated with applications, products, accessories, services, or some combination thereof, that are used to, e.g., create content in an artificial reality and/or are otherwise used in (e.g., perform activities in) an artificial reality. The artificial reality system that provides the artificial reality content may be implemented on various platforms, including a head-mounted display (HMD) connected to a host computer system, a standalone HMD, a mobile device or computing system, or any other hardware platform capable of providing artificial reality content to one or more viewers.

The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed. The various exemplary methods described and/or illustrated herein may also omit one or more of the steps described or illustrated herein or include additional steps in addition to those disclosed.

The preceding description has been provided to enable others skilled in the art to best utilize various aspects of the exemplary embodiments disclosed herein. This exemplary description is not intended to be exhaustive or to be limited to any precise form disclosed. Many modifications and variations are possible without departing from the spirit and scope of the instant disclosure. The embodiments disclosed herein should be considered in all respects illustrative and not restrictive. Reference should be made to the appended claims and their equivalents in determining the scope of the instant disclosure.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and have the same meaning as the word "comprising."

What is claimed is:

1. A head-mounted display apparatus comprising:
   a left display subsystem and a right display subsystem, wherein the left and right display subsystems each comprise:
      a display screen; and
      a lens configured to focus light from the display screen at an exit pupil of the head-mounted display apparatus;
   an actuation subsystem configured to change relative positioning of the left and right display subsystems based on received data indicative of an inter-pupillary distance of a user; and a detection subsystem configured to identify the inter-pupillary distance of the user while the user is wearing the head-mounted display apparatus, wherein the detection subsystem is configured to measure the inter-pupillary distance of the user by:
projecting a dot pattern onto each eye of the user;
analyzing a reflection of the dot pattern from each eye of the user to identify a location of each pupil of the user; and
comparing the location of each pupil of the user to calculate the inter-pupillary distance.

2. The head-mounted display apparatus of claim 1, wherein the actuation subsystem is in communication with and receives the data indicative of the inter-pupillary distance of the user from the detection subsystem.

3. The head-mounted display apparatus of claim 2, wherein the detection subsystem is configured to measure the inter-pupillary distance of the user while the user is wearing the head-mounted display apparatus.

4. The head-mounted display apparatus of claim 1, wherein the actuation subsystem comprises:
a first actuator coupled to the left display subsystem and configured to move the left display subsystem independent of the right display subsystem; and
a second actuator coupled to the right display subsystem and configured to move the right display subsystem independent of the left display subsystem.

5. The head-mounted display apparatus of claim 1, wherein the actuation subsystem comprises a single actuator configured to move the left and right display subsystems at least substantially simultaneously.

6. The head-mounted display apparatus of claim 1, wherein:
the actuation subsystem comprises a motor;
the actuation subsystem comprises a drive mechanism that couples the motor to at least one of the left and right display subsystems such that driving by the motor causes the drive mechanism to move the at least one of the left and right display subsystems; and
the motor changes the relative positioning by causing the drive mechanism to move at least one of the left and right display subsystems.

7. The head-mounted display apparatus of claim 6, wherein the motor comprises a stepper motor.

8. The head-mounted display apparatus of claim 6, wherein the drive mechanism comprises:
a pinion secured to the motor; and
a rack driven by the pinion and secured to the at least one of the left and right display subsystems to which the drive mechanism is coupled.

9. The head-mounted display apparatus of claim 6, wherein:
a left portion of the drive mechanism comprises a first thread that interfaces with the left display subsystem;
a right portion of the drive mechanism comprises a second thread that interfaces with the right display subsystem; and
the second thread comprises a helix that twists in an opposite direction of a helix of the first thread such that rotation of the drive mechanism moves the left and right display subsystems in opposite directions.

10. The head-mounted display apparatus of claim 1, wherein each of the left and right display subsystems comprise a varifocal subsystem configured to move the display screen relative to the lens to change a focal length of the lens.

11. The head-mounted display apparatus of claim 1, further comprising a linear track positioned to guide lateral movement of at least one of the left and right display subsystems as the actuation subsystem changes the relative positioning of the left and right display subsystems.

12. The head-mounted display apparatus of claim 1, further comprising a nonlinear track positioned to guide angular movement of at least one of the left and right display subsystems as the actuation subsystem changes the relative positioning of the left and right display subsystems.

13. The head-mounted display apparatus of claim 1, wherein the actuation subsystem changes the relative positioning of the left and right display subsystems by rotating at least one of the left and right display subsystems.

14. The head-mounted display apparatus of claim 1, further comprising a housing within which the left and right display subsystems are disposed, wherein the actuation subsystem comprises:
an actuator mounted to the housing; and
a drive mechanism coupled to the actuator and coupled to at least one of the left display subsystem and the right display subsystem.

15. A method comprising:
identifying an inter-pupillary distance of a user of a head-mounted display apparatus; and
directing an actuation subsystem to change relative positioning of left and right display subsystems of the head-mounted display apparatus based on the identified inter-pupillary distance of the user, wherein the left and right display subsystems each comprise:
a display screen; and
a lens configured to focus light from the display screen at an exit pupil of the head-mounted display apparatus,
wherein directing the actuation subsystem to change the relative positioning of the left and right display subsystems comprises activating a motor coupled to a drive mechanism, wherein the drive mechanism couples the motor to the left display subsystem with a first thread having a first helix that twists in a first direction and to the right display subsystem with a second thread having a second helix that twists in a second, opposite direction such that rotation of the drive mechanism with the motor moves the left and right display subsystems in opposite directions.

16. The method of claim 15, wherein the identifying the inter-pupillary distance comprises measuring the inter-pupillary distance of the user while the user is wearing the head-mounted display apparatus.

17. The method of claim 16, wherein the measuring the inter-pupillary distance comprises:
directing an illumination source to project a dot pattern onto each eye of the user;
analyzing a reflection of the dot pattern from each eye of the user to identify a location of each pupil of the user; and
comparing the location of each pupil of the user to calculate the inter-pupillary distance.

18. The method of claim 15, wherein the actuation subsystem comprises:
a first actuator coupled to the left display subsystem and configured to move the left display subsystem independent of the right display subsystem; and
a second actuator coupled to the right display subsystem and configured to move the right display subsystem independent of the left display subsystem.

19. A method comprising:
securing a left display subsystem to a housing of a head-mounted display apparatus, wherein the left display subsystem comprises:
- a left display screen; and
- a left lens configured to focus light from the left display screen at a left exit pupil of the head-mounted display apparatus;

securing a right display subsystem to the housing of the head-mounted display apparatus, wherein the right display subsystem comprises:
- a right display screen; and
- a right lens configured to focus light from the right display screen at a right exit pupil of the head-mounted display apparatus; and coupling, to at least one of the left and right display subsystems, an actuation subsystem configured to change relative positioning of the left and right display subsystems based on received data indicative of an inter-pupillary distance of a user, wherein the coupling of the actuation subsystem to at least one of the left and right display subsystems comprises coupling a first thread having a first helix that twists in a first direction to the left display subsystem and coupling a second thread having a second helix that twists in a second, opposite direction to the right display subsystem.

* * * * *

UNITED STATES PATENT AND TRADEMARK OFFICE
CERTIFICATE OF CORRECTION

| | | |
|---|---|---|
| PATENT NO. | : 10,701,350 B1 | Page 1 of 1 |
| APPLICATION NO. | : 16/014447 | |
| DATED | : June 30, 2020 | |
| INVENTOR(S) | : Ryan Michael Ebert | |

It is certified that error appears in the above-identified patent and that said Letters Patent is hereby corrected as shown below:

On the Title Page

In Column 1, item (71), Applicant, Line 1, delete "Oculus VR, LLC" and insert -- Facebook Technologies, LLC --, therefor.

Signed and Sealed this
First Day of September, 2020

Andrei Iancu
*Director of the United States Patent and Trademark Office*